United States Patent
Allais et al.

(10) Patent No.: US 8,735,607 B2
(45) Date of Patent: May 27, 2014

(54) PROCESS FOR THE PRODUCTION OF ALKYLENE CARBONATE

(75) Inventors: Cyrille Paul Allais, Amsterdam (NL); Evert Van Der Heide, Amsterdam (NL); Gerardus Martinus Maria Van Kessel, Amsterdam (NL)

(73) Assignee: Shell Oil Company, Houston, TX (US)

( * ) Notice: Subject to any disclaimer, the term of this patent is extended or adjusted under 35 U.S.C. 154(b) by 791 days.

(21) Appl. No.: 12/993,136

(22) PCT Filed: May 19, 2009

(86) PCT No.: PCT/EP2009/056098
§ 371 (c)(1),
(2), (4) Date: Jan. 18, 2011

(87) PCT Pub. No.: WO2009/141361
PCT Pub. Date: Nov. 26, 2009

(65) Prior Publication Data
US 2011/0108762 A1  May 12, 2011

(30) Foreign Application Priority Data

May 20, 2008  (EP) .................................... 08156515

(51) Int. Cl.
*C07D 317/36* (2006.01)
*C07D 317/38* (2006.01)

(52) U.S. Cl.
CPC ............ *C07D 317/36* (2013.01); *C07D 317/38* (2013.01)
USPC ........................................................ 549/230

(58) Field of Classification Search
CPC ............................ C07D 317/36; C07D 317/38
USPC ........................................................... 549/230
See application file for complete search history.

(56) References Cited

U.S. PATENT DOCUMENTS

| | | | |
|---|---|---|---|
| 2,994,705 A | 8/1961 | Crosby et al. | 260/340.2 |
| 4,314,945 A | 2/1982 | McMullen et al. | 260/340.2 |
| 4,434,105 A | 2/1984 | Buysch et al. | 260/463 |
| 4,691,041 A | 9/1987 | Duranleau et al. | 558/277 |
| 5,153,333 A | 10/1992 | Schubert et al. | 549/230 |
| 5,231,212 A | 7/1993 | Buysch et al. | 558/277 |
| 5,359,118 A | 10/1994 | Wagner et al. | 558/277 |
| 2003/0212280 A1 | 11/2003 | Kahn | 549/230 |

FOREIGN PATENT DOCUMENTS

| | | | |
|---|---|---|---|
| EP | 776890 | 6/1997 | C07D 317/38 |
| WO | WO9957108 | 11/1999 | C07D 317/36 |
| WO | WO0020407 | 4/2000 | C07D 317/36 |
| WO | WO0166510 | 9/2001 | C07C 68/00 |
| WO | WO2004063183 | 7/2004 | C07D 317/36 |
| WO | WO2005003113 | 1/2005 | C07D 317/36 |
| WO | WO2007104730 | 9/2007 | C07D 317/36 |

*Primary Examiner* — Noble Jarrell
*Assistant Examiner* — Valerie Rodriguez-Garcia

(57) ABSTRACT

The invention relates to a process for the production of an alkylene carbonate by the reaction of an alkylene oxide with carbon dioxide in the presence of a phosphonium catalyst in which process (a) the alkylene oxide, carbon dioxide and phosphonium catalyst are continuously introduced into a reaction zone from which a product stream containing alkylene carbonate and phosphonium catalyst is withdrawn; (b) alkylene carbonate and a stream containing phosphoniura catalyst are separated from the product stream; (c) the alkylene carbonate, separated in step (b), is recovered as product; and (d) the stream containing phosphoniura catalyst, separated in step (b), is recycled to the reaction zone, in which process a treatment of alkylene carbonate and/or catalyst with a sorption agent comprising carbon is carried out.

12 Claims, 1 Drawing Sheet

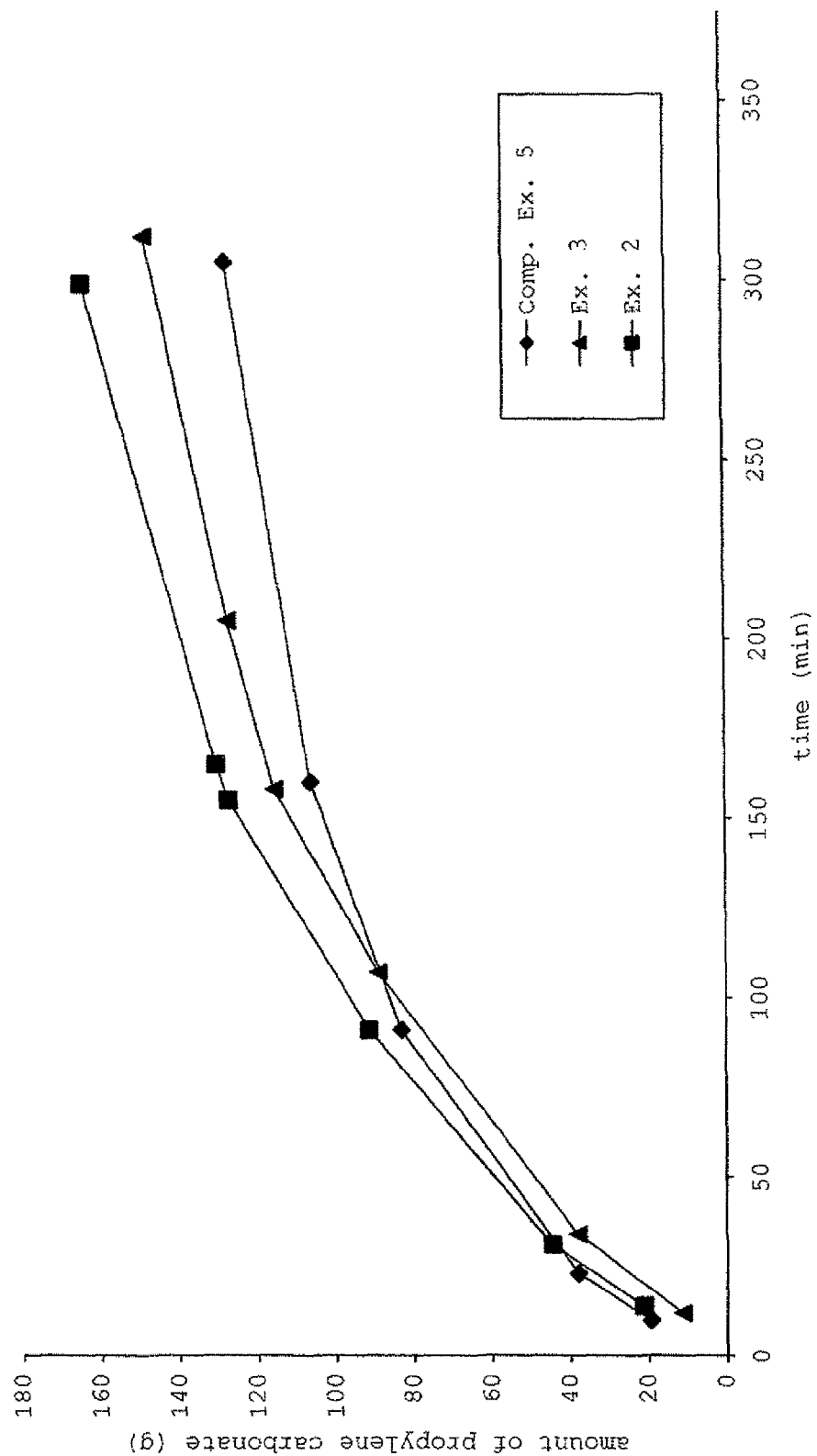

PROCESS FOR THE PRODUCTION OF ALKYLENE CARBONATE

PRIORITY CLAIM

The present application claims priority to European Patent Application No. 08156515.2 filed 20 May 2008.

The present invention relates to a process for the production of alkylene carbonate.

Processes for the production of alkylene carbonates are known. WO-A 2005/003113 discloses a process in which carbon dioxide is contacted with an alkylene oxide in the presence of a suitable catalyst. The catalyst disclosed is a tetraalkyl phosphonium compound. WO-A 2005/003113 discloses that the catalyst used has been recycled. U.S. Pat. No. 4,434,105 also discloses a process for the preparation of alkylene carbonates. Various catalysts are disclosed. U.S. Pat. No. 4,434,105 also describes that the catalyst after completion of the reaction may be reused.

In a continuous process the reaction product containing alkylene carbonate and catalyst has to be subjected to a work-up treatment. Such work-up treatment generally includes distillation to separate the alkylene carbonate product from the catalyst. According to WO-A 2007/104730, it was found in a continuous alkylene carbonate production process using a phosphonium catalyst, that the activity of the catalyst decreases if the catalyst is being reused without taking appropriate steps to remove contaminants therefrom. Therefore, WO-A 2007/104730 proposes that the used catalyst is purified before it is recycled.

The contaminants which are removed according to said WO-A 2007/104730, are decomposition products of the phosphonium catalyst, such as phosphine oxides. By removing the latter contaminants, a build-up of these contaminants in the continuous process is avoided. In Example 1 of WO-A 2007/104730, a catalyst solution comprising both propylene carbonate and used phosphonium catalyst (tetrabutyl phosphonium bromide; $Bu_4PBr$), also containing some tributyl phosphine oxide (i.e. $Bu_3P=O$), was subjected to distillation. Two consecutive distillations were needed to first remove the propylene carbonate and then to remove most of the tributyl phosphine oxide. The residue consisted mainly of the tetrabutyl phosphonium bromide.

The insertion of carbon dioxide into the oxirane moiety of alkylene oxides is a reversible reaction. That is to say, alkylene oxide may also be formed back from alkylene carbonate under release of carbon dioxide. It is expected that some contaminants which are formed during the production of alkylene carbonate and/or the work-up of the alkylene carbonate containing reaction mixture, may catalyze such back-reaction.

Above-mentioned WO-A 2007/104730 does not mention the removal of contaminants which may catalyze the back-reaction of alkylene carbonate into alkylene oxide and carbon dioxide. Further, the present inventors have found that phosphine oxides do not catalyze such back-reaction, which is demonstrated in the Examples below.

The object of the present invention is to provide a continuous process for the production of an alkylene carbonate from an alkylene oxide and carbon dioxide using a phosphonium catalyst which is recycled in the process, wherein the back-reaction of alkylene carbonate into alkylene oxide and carbon dioxide is prevented as much as possible and the recovery of alkylene carbonate can therefore be maximised.

Surprisingly, it was found that this object is achieved by carrying out, in said continuous alkylene carbonate production process using recycled catalyst, a treatment of alkylene carbonate and/or catalyst with a sorption agent comprising carbon.

Accordingly, the present invention relates to a process for the production of an alkylene carbonate by the reaction of an alkylene oxide with carbon dioxide in the presence of a phosphonium catalyst in which process (a) the alkylene oxide, carbon dioxide and phosphonium catalyst are continuously introduced into a reaction zone from which a product stream containing alkylene carbonate and phosphonium catalyst is withdrawn;
(b) alkylene carbonate and a stream containing phosphonium catalyst are separated from the product stream;
(c) the alkylene carbonate, separated in step (b), is recovered as product; and
(d) the stream containing phosphonium catalyst, separated in step (b), is recycled to the reaction zone,
in which process a treatment of alkylene carbonate and/or catalyst with a sorption agent comprising carbon is carried out.

In above-mentioned WO-A 2007/104730, it is suggested that before recycling the used phosphonium catalyst, it is purified by subjecting it to adsorption. However, specific sorption agents are not mentioned in WO-A 2007/104730. The present inventors, on the other hand, have tested a variety of sorption agents and surprisingly found that a sorption agent comprising carbon gave the best results in terms of preventing the back-reaction of alkylene carbonate into alkylene oxide and carbon dioxide and maximising the recovery of alkylene carbonate, which is demonstrated in the Examples below. A further advantage of the present process resides in the fact that the process pre-empts the necessity to include a bleed stream via which any contaminants catalyzing said back-reaction, have to be withdrawn from the process.

In Comparative Examples 2 and 3 of US20030212280, high surface area carbon (1100 and 1350 $m^2/g$, respectively) is used to treat propylene carbonate that contains N and Br species.

In the present specification, sorption means a process in which one substance (the sorption agent) takes up or holds another substance by absorption, adsorption or a combination of both.

In the present process, the sorption agent to be used in the sorption treatment comprises carbon. Said sorption agent comprising carbon may be a carrier which carries carbon on its internal and/or external surfaces. Preferably, said carrier comprises an inorganic oxide, for example aluminum oxide ($Al_2O_3$ or alumina), silicon oxide ($SiO_2$ or silica) or titanium oxide ($TiO_2$ or titania).

Preferably, said sorption agent comprising carbon is a substance which mainly consists of carbon, for example a substance comprising 80 to 100 wt. % of carbon, preferably 90 to 100 wt. % of carbon, more preferably 95 to 100 wt. % of carbon, most preferably 98 to 100 wt. % of carbon, and highly preferably 99 to 100 wt. % of carbon. An example of such substance which mainly consists of carbon and which is an especially preferred sorption agent in the present process, is active carbon, also referred to in the art as activated carbon, active (char)coal or activated (char)coal. Said active carbon is a substance which contains macropores (pore diameter >50 nm), mesopores (pore diameter 2-50 nm) and micropores (pore diameter <2 nm), and which comprises of from 99 to 100 wt. % of carbon and has a surface area (internal and external) of from 100 to 2000 $m^2/g$ as determined by nitrogen gas adsorption. Preferably, the surface area of the active carbon which may be used as the sorption agent in the present process, is of from 500 to 1500 $m^2/g$.

The sorption agent to be used in the present process may have a particle size over a broad range, and can have any shape. For example, said sorption agent may have a particle diameter <0.18 mm (e.g. powdered activated carbon) or a particle diameter in the range of from 0.2 to 0.7 mm (e.g. granulated activated carbon) or a particle diameter in the range of from 0.8 to 5 mm (e.g. extruded activated carbon).

The treatment of alkylene carbonate and/or catalyst with the sorption agent comprising carbon may be carried out anywhere in and any time during the present process. For example:
(i) said treatment may be carried out during the production of alkylene carbonate in the reaction zone in step (a); and/or
(ii) said treatment may be carried out during the separation in step (b); and/or
(iii) the stream containing catalyst separated in step (b) may be subjected to said treatment before said stream is recycled to the reaction zone; and/or
(iv) alkylene carbonate separated in step (b) may be subjected to said treatment before the alkylene carbonate is recovered in step (c).

With any of these treatments with the sorption agent comprising carbon, it is possible to prevent back-reaction of alkylene carbonate into alkylene oxide and carbon dioxide as much as possible. Further, the sorption agent to be used in the present process, may be suspended or fixed.

Therefore, the sorption agent may be suspended (or slurried) in the reaction mixture that is present in the reaction zone or reactor in step (a) in the present process. Further, the sorption agent may be suspended in the product stream which in step (b) of the present process, is separated into alkylene carbonate and a stream containing phosphonium catalyst. Such separation may be carried out by distillation in a distillation column, as is further discussed below. In the latter case, the sorption agent may be suspended in the distillation column. In general, if after treatment with a suspended sorption agent, the sorption agent needs to be removed from a particular stream or mixture, this may be achieved by filtering.

Still further, the sorption agent may be suspended in the stream containing phosphonium catalyst separated in said step (b) before it is recycled, in step (d) of the present process, to the reaction zone in step (a). For example, the separated stream containing phosphonium catalyst may be stored in a vessel before it is recycled to the reaction zone in step (a). In the latter case, the sorption agent may be suspended in the (storage) vessel. After treatment with the sorption agent, the suspended sorption agent may be removed, e.g. by filtering. Alternatively, the suspended sorption agent may be sent to the reaction zone in step (a).

The sorption agent may also be suspended in any part of the lines and pipings that connect the reaction zone, reactor, distillation column and/or (storage) vessel as discussed above, as long as such part of a line or piping is bounded both downstream and upstream by a membrane through which the sorption agent cannot permeate but through which the reactants and/or products and/or any solvent can permeate.

In all of the foregoing cases, the sorption agent may be fixed rather than suspended, which means that the reaction zone, reactor, distillation column and/or (storage) vessel, or part thereof, and/or part of a line or piping as discussed above, is filled with such amount of sorption agent that the sorption agent becomes fixed (immobile) rather than suspended (mobile).

Still further, it is envisaged that in all of the foregoing cases, a portion of the mixture containing reactants and/or products and/or catalyst in question, i.e. not the entire mixture in question, is treated with the sorption agent comprising carbon. This also results in the advantages of the present invention, as by doing so the build-up of any contaminants catalyzing the back-reaction of alkylene carbonate into alkylene oxide and carbon dioxide, is avoided. Suitably, such portion represents of from 1 to 90% wt, more preferably from 2 to 50% wt, most preferably from 5 to 25% wt of the mixture in question.

The catalyst is a phosphonium compound. Such catalysts are known, e.g. from U.S. Pat. No. 5,153,333, U.S. Pat. No. 2,994,705, U.S. Pat. No. 4,434,105, WO-A 99/57108, EP-A 776,890, WO-A 2005/003113 and WO-A 2007/104730. Preferably, the catalyst is a phosphonium halide of formula $(R)_4PX$, in which X means halide and each R can be the same or different and can be selected from an alkyl, alkenyl, cyclic aliphatic or an aromatic group. The group R suitably contains from 1 to 12 carbon atoms. Good results are obtained with R being a $C_{1-8}$ alkyl group. Most preferred are groups R being selected from methyl, ethyl, n-propyl, isopropyl, n-butyl, isobutyl, and t-butyl groups. Preferably, the halide ion is bromide or iodide. It appeared that the bromide and iodide compounds are more stable than the corresponding chloride compounds. The most preferred phosphonium catalyst is tetra (n-butyl) phosphonium bromide.

In step (d) of the present process, a stream containing phosphonium catalyst is recycled to the reaction zone in step (a). Since the presence of a solvent shows a stabilising effect on the catalyst it is preferred to recycle the phosphonium catalyst to the reaction zone in the presence of a solvent. This solvent may be an alcohol. Suitable alcohol solvents are alkylene diols, in particular ethanediol or propanediol. The use of ethanediol or propanediol has a further advantage when the alkylene carbonate is converted to alkylene glycol (alkanediol), and the alkylene glycol is used as solvent for the catalyst.

The phosphonium catalyst containing recycle stream to step (a) suitably contains some alkylene carbonate. The alkylene carbonate ensures that the phosphonium catalyst is in liquid form, which facilitates transportation. Further, in a case where an alcohol is used as solvent for the catalyst, the combination of said alcohol and alkylene carbonate has a stabilising effect on the catalyst.

The amount of catalyst in the reactor or reaction zone in step (a) may conveniently be expressed in mole catalyst per mole alkylene oxide. Due to a lower amount of by-products, the carbonation is suitably carried out in the presence of at least 0.0001 mole of the catalyst per mole alkylene oxide. Preferably, the amount of catalyst present is such that it ranges from 0.0001 to 0.1 mole catalyst, more preferably from 0.001 to 0.05, and most preferably from 0.003 to 0.03 mole catalyst per mole alkylene oxide.

The alkylene oxide that is contacted with the carbon dioxide in step (a) of the present process, is suitably a $C_{2-4}$ alkylene oxide, preferably ethylene oxide and/or propylene oxide, or mixtures of such $C_{2-4}$ alkylene oxides. Where ethylene oxide is used, the produced alkylene carbonate is ethylene carbonate. Where propylene oxide is used, the produced alkylene carbonate is propylene carbonate.

As mentioned above, the reaction of carbon dioxide with the alkylene oxide is reversible. That means that the alkylene carbonate formed may convert back into carbon dioxide and the alkylene oxide. In step (a) of the present process, the molar ratio between carbon dioxide and alkylene oxide may be as low as 0.5:1, more suitably from 0.75:1. However, in view of the reversibility of the reaction it is preferred to ensure at least a slight excess of carbon dioxide, such as 1.0:1 to 10:1, more preferably from 1.01:1 to 2:1, most preferably from 1.01:1 to 1.2:1. A suitable means to establish an excess of carbon dioxide is to conduct the reaction at an elevated carbon dioxide pressure and keeping the pressure constant by dosing carbon dioxide. The total pressure ranges suitably from 5 to 200 bar; the partial carbon dioxide partial pressure is preferably in the range from 5 to 70, more preferably from 7 to 50, and most preferably from 10 to 30 bar.

The reaction temperature in step (a) of the present process can be selected from a wide range. Suitably the temperature is selected from 30 to 300° C. The advantage of relatively high temperature is the increase in reaction rate. However, if the reaction temperature is too high, side reactions may occur, or the undesired decomposition of the catalyst may be accelerated. Therefore, the temperature is suitably selected from 100 to 220° C.

The skilled person will be able to adapt other reaction conditions as appropriate. The residence time of the alkylene oxide and the carbon dioxide in the reactor or reaction zone in step (a) of the present process can be selected without undue burden. The residence time can usually be varied between 5 min and 24 hours, preferably between 10 minutes and 10 hours. Conversion of alkylene oxide is suitably at least 95%, more preferably at least 98%. Dependent on the temperature and pressure the residence time may be adapted. The catalyst concentration may also vary between wide ranges. Suitable concentrations include from 1 to 25% wt, based on the total reaction mixture. Good results can be obtained with a catalyst concentration of 2 to 8% wt, based on the total reaction mixture.

In step (a) of the present process, only one reactor may be used. However, it is also feasible to carry out the reaction of step (a) in two or more reactors. In such cases it may be advantageous to provide for the optimal amount of excess carbon dioxide in the reactors by removing or adding carbon dioxide between the reactors. The reactors are suitably conducted under plug flow conditions. It is even more preferred to have a back-mix reactor, e.g. a Continuously Stirred Tank Reactor (CSTR), followed by a plug-flow reactor. Such a combination is known from e.g. U.S. Pat. No. 4,314,945.

The desired product alkylene carbonate may be recovered from the product mixture originating from step (a) in the following way. First of all, carbon dioxide and light components may be separated from the crude reactor effluent from said step (a) in one or more gas-liquid separators to form a bottoms stream containing alkylene carbonate and catalyst. Said light components are compounds, other than carbon dioxide, which have a boiling point which is 185° C. or lower, more specifically 180° C. or lower. Examples of such light components in the crude effluent from the carbonation reactor may be unreacted alkylene oxide and any light contaminants formed during the carbonation reaction, such as acetone, propionaldehyde, allyl alcohol and acetaldehyde.

Following the removal of said unreacted carbon dioxide and light components, alkylene carbonate and a stream containing phosphonium catalyst are to be separated in accordance with step (b) of the present process. This may be achieved by sending the above-mentioned bottoms stream containing alkylene carbonate and catalyst to a distillation column where it is distilled to form a first distillation overhead stream and a first distillation bottoms stream. The first distillation overhead stream contains alkylene carbonate. The first distillation bottoms stream contains catalyst and possibly some alkylene carbonate. The first distillation bottoms stream is partially or completely recycled to the reactor in accordance with step (d) of the present process.

In a situation where an alcohol is used as a solvent for the catalyst and such alcohol has a lower boiling point than the alkylene carbonate, as is the case when the alcohol used is propanediol and the alkylene carbonate is propylene carbonate or when the alcohol used is ethanediol and the alkylene carbonate is ethylene carbonate, the first distillation overhead stream contains said alcohol in addition to alkylene carbonate.

As to the way the distillation may be performed in order to separate catalyst from alkylene carbonate and any alcohol used as solvent for the catalyst, the skilled artisan can vary the temperature and number of trays without undue burden.

In accordance with step (c) of the present process, the alkylene carbonate, separated in step (b), is recovered as product. This may be achieved as follows. The above-mentioned first distillation overhead stream may be distilled to form a second distillation overhead stream and a second distillation bottoms stream. The second distillation bottoms stream contains alkylene carbonate, i.e. the purified end product.

In a situation where an alcohol is used as a solvent for the catalyst and such alcohol has a lower boiling point than the alkylene carbonate, the distillation of the first distillation overhead stream should be carried out such that the second distillation overhead stream contains said alcohol and the final alkylene carbonate product contains no or substantially no alcohol.

As to the way the distillation of the first distillation overhead stream may be performed in order to separate alkylene carbonate from any alcohol used as solvent for the catalyst, the skilled artisan can vary the temperature and number of trays without undue burden.

The alkylene carbonate that is produced in the present process can suitably be used for the production of alkanediol and dialkylcarbonate. Accordingly, in the process of the present invention preferably (e) the alkylene carbonate recovered as product in step (c) is contacted with an alkanol to obtain a reaction mixture containing an alkylene dial and a dialkylcarbonate; and (f) alkylene diol and dialkylcarbonate are recovered.

The alkanol used in above transesterification step (v) is suitably a $C_{1-4}$ alcohol. Preferably, the alkanol is methanol, ethanol or isopropanol. Said step (v) may be performed in the presence of a heterogeneous transesterification catalyst.

The transesterification reaction in itself is known. In this context reference is made to U.S. Pat. No. 4,691,041, disclosing a process for the manufacture of ethylene glycol and dimethyl carbonate by the transesterification reaction over a heterogeneous catalyst system, in particular an ion exchange resin with tertiary amine, quaternary ammonium, sulphonic acid and carboxylic acid functional groups, alkali and alkaline earth silicates impregnated into silica and ammonium exchanged zeolites. U.S. Pat. No. 5,359,118 and U.S. Pat. No. 5,231,212 disclose a continuous process for preparing dialkyl carbonates over a range of catalysts, including alkali metal compounds, in particular alkali metal hydroxides or alcoholates, such as sodium hydroxide or methanolate, thallium compounds, nitrogen-containing bases such as trialkyl amines, phosphines, stibines, arsenines, sulphur or selenium compounds and tin, titanium or zirconium salts. According to WO-A 2005/003113 the reaction of alkylene carbonate with an alkanol is conducted over heterogeneous catalysts, e.g. alumina.

The invention is further illustrated by the following Examples.

Example 1 and Comparative Examples 1-4

In these experiments, it was investigated to what extent the back-reaction of propylene carbonate into propylene oxide and carbon dioxide took place, in the presence of a tetrabutyl phosphonium bromide catalyst that previously had been used in the preparation of propylene carbonate from propylene oxide and carbon dioxide and that after said use either had not been pretreated with a sorption agent (Comp. Ex. 1) or had been pretreated with a sorption agent (Comp. Ex. 2-4 and Ex. 1).

In those experiments wherein the used tetrabutyl phosphonium bromide catalyst had been pretreated with a sorption agent, such pretreatment was performed at room temperature in a closed glass bottle containing a slurry consisting of a catalyst solution and a sorption agent. The composition of said solution, said sorption agent, the amount of said solution, the amount of said sorption agent and the duration of the pretreatment are indicated in Table 1 below. During the pretreatments, the slurries in the glass bottles were mixed on a roller bank.

TABLE 1

Catalyst pretreatments with sorption agent

| (Comp.) Ex. | Weight of catalyst solution[1] (g) | Sorption agent | Weight of sorption agent (g) | Duration of pretreatment (h) |
|---|---|---|---|---|
| Comp. Ex. 2 | 50 | silica[2] | 5 | 1 |
| Comp. Ex. 3 | 50 | alumina[3] | 5 | 1 |
| Comp. Ex. 4 | 81 | magnesium silicate[4] | 7.5 | 2 |
| Ex. 1 | 82 | activated carbon[5] | 10 | 1 |

[1]The catalyst solution consisted of: 67.6 wt. % of propylene carbonate, 24.9 wt. % of the used tetrabutyl phosphonium bromide catalyst, 7.2 wt. % of tributyl phosphine oxide and 0.3 wt. % of monopropylene glycol.
[2]Silicon dioxide nanopowder (10 nm - Aldrich - 99.5%).
[3]X-227 γ-alumina (ex CRI Criterion).
[4]AMBOSOL magnesium silicate (ex Clarian).
[5]SXPL03 powdered activated carbon (ex Norit).

As can be derived from Table 1 above, during all of the pretreatments, the weight ratio of the sorption agent to the catalyst solution was about 0.1. At the end of the pretreatments, the sorption agent was separated by filtering the slurries. Stability tests were then performed on the filtrates thus obtained (Comp. Ex. 2-4 and Ex. 1). A stability test was also performed on 99.6 g of a catalyst solution having the composition as described above below Table 1, but which had not been pretreated with a sorption agent (Comp. Ex. 1).

In said stability tests, the temperature was 150° C., the pressure was approximately 105 mbar, and the test duration was approximately 18 hours. Said tests were carried out in magnetically stirred vessels (about 100 rpm). Further, the experimental set-up used was such that light components formed during the tests, including propylene oxide and derivatives thereof (such as propionaldehyde, acetone, allyl alcohol and bromohydrin), were distilled off from said vessels and cold-trapped at about −78° C. in a container having a double wall filled with a mixture of dry ice and acetone.

Both at the beginning and at the end of the stability tests, the weight of the contents of the vessel was determined. Then the percentage of the final weight on the basis of the original weight was determined, which is indicated in Table 2 below as "Reside".

TABLE 2

Stability tests

| (Comp.) Ex. | Sorption agent used during pretreatment (see also Table 1) | Residu (wt. %) |
|---|---|---|
| Comp. Ex. 1 | none | 82.3 |
| Comp. Ex. 2 | silica | 67.0 |
| Comp. Ex. 3 | alumina | 67.0 |
| Comp. Ex. 4 | magnesium silicate | 35.8 |
| Ex. 1 | activated carbon | 83.5 |

From Table 2 above it appears that 82.3% of the original weight of the mixture which had not been pretreated with a sorption agent (Comp. Ex. 1) was still present in the vessel at the end of the stability test. And further it appears that of the mixture which had been pretreated with activated carbon as a sorption agent (Ex. 1), a higher percentage (i.e. 83.5%) of the original weight was still present in the vessel at the end of the stability test. This means that in the case where the used catalyst had been pretreated with activated carbon as a sorption agent (Ex. 1), surprisingly less back-reaction of propylene carbonate into propylene oxide and carbon dioxide took place than in the case where no pretreatment with a sorption agent had been performed (Comp. Ex. 1).

Further, and even more surprisingly, it appeared that in those cases where the used catalyst had been pretreated with sorption agents other than activated carbon (Comp. Ex. 2-4), more back-reaction of propylene carbonate into propylene oxide and carbon dioxide took place than in the case where no pretreatment with a sorption agent had been performed (Comp. Ex. 1), as indicated by a relatively low value for "Residu" for Comp. Ex. 2-4 in Table 2 above. Therefore, silica, alumina and magnesium silicate are not suitable for use as a sorption agent for treating tetrabutyl phosphonium bromide catalyst that has been used in making propylene carbonate from propylene oxide and carbon dioxide, in order to reduce the back-reaction of the propylene carbonate.

Reference Example

As mentioned above, WO-A 2007/104730 discloses purifying a phosphonium catalyst that has been used in a continuous alkylene carbonate production process, such that the catalyst decomposition product which comprises phosphine oxide is removed therefrom, before recycle of the catalyst. The aim of the experiments in this example is to investigate whether or not phosphine oxides catalyze the back-reaction of alkylene carbonate into alkylene oxide and carbon dioxide.

A stability test was performed on a mixture consisting of 74.7 g of propylene carbonate and 26.7 g of tetrabutyl phosphonium bromide catalyst. Further, a stability test was performed on a mixture consisting of 67.0 g of propylene carbonate, 25.2 g of tetrabutyl phosphonium bromide catalyst and 7.0 g of tributyl phosphine oxide.

In said stability tests, the temperature was 150° C., the pressure was 100 mbar, and the test duration was 20 hours. Said tests were carried out in magnetically stirred vessels (about 100 rpm). Further, the experimental set-up used was such that light components formed during the tests, including propylene oxide and derivatives thereof (such as propionaldehyde, acetone, allyl alcohol and bromohydrin), were distilled off from said vessels and cold-trapped at about −78° C. in a container having a double wall filled with a mixture of dry ice and acetone.

At the end of said stability tests, the weight of the contents of the vessel was determined. For both said tests, it appeared that 95.1% of the original weight of the mixtures was still present in the vessel at the end of the test. This indicates that tributyl phosphine oxide does not catalyze the back-reaction of propylene carbonate into propylene oxide and carbon dioxide.

Examples 2-3 and Comparative Example 5

In these experiments, the activity of a tetrabutyl phosphonium bromide catalyst in the preparation of propylene carbonate from propylene oxide and carbon dioxide was investigated. Said catalyst had previously also been used in the preparation of propylene carbonate from propylene oxide and carbon dioxide. After said previous use, the catalyst either had not been pretreated with a sorption agent (Ex. 3 and Comp. Ex. 5) or had been pretreated with activated carbon as a sorption agent (Ex. 2). Further, said experiments in Ex. 3 and Comp. Ex. 5 differed from each other in that in the experiment of Ex. 3 activated carbon was used as a sorption agent during the experiment.

The experiments were carried out in a 1-liter stainless steel autoclave reactor. The temperature in the reactor was controlled by an oil bath, the pressure was controlled with an automatic pressure controller that regulated the intake of carbon dioxide ($CO_2$). The reactor was equipped with a hollow shaft stirrer to enhance gas-liquid contact. A dip pipe was installed for sampling.

The reactor was loaded with 120 g of propylene oxide (PO) and 3 g of sulfolane (internal standard). $CO_2$ was added to raise the pressure to approximately 4 bar. The mixture was heated to 145° C. and $CO_2$ was added to reach the desired reaction pressure of 20 bar. 2.4 g of a catalyst solution, containing 2 g of propylene carbonate and 250 mg of the used tetrabutyl phosphonium bromide catalyst (the remainder being tributyl phosphine oxide), was used in each experiment.

In the experiment of Ex. 2, the catalyst solution used had been pretreated with activated carbon as a sorption agent. Said pretreatment involved treatment of 10 g of the above catalyst solution with 1 g of activated carbon (SXPL03 powdered activated carbon; ex Norit) for 16 hours on a roller bank at room temperature, followed by filtration of the slurry. 2.4 g of the filtrate thus obtained was used as the catalyst solution in the experiment of Ex. 2.

In each experiment, monopropylene glycol (MPG) was added to the catalyst solution: 14.0 g of MPG in Ex. 2, 14.5 g of MPG in Ex. 3 and 15.1 g of MPG in Comp. Ex. 5. The solution thus obtained was then injected into the reactor. In the experiment of Ex. 3, 233 mg of activated carbon (SXPL03 powdered activated carbon; ex Norit) were also injected as a sorption agent into the reactor together with injecting said catalyst solution.

Temperature and pressure were kept constant at 150° C. and 20 bar, respectively, during the entire experiments. Samples from the reaction mixture were taken with increasing time interval, in order to measure, by means of gas chromatography, the amount of propylene carbonate formed in the reaction mixture. In FIG. 1, the amount of propylene carbonate is plotted against time for each experiment.

From FIG. 1, it appears that the activity of the catalyst is lowest when the catalyst is not pretreated with activated carbon and such activated carbon is neither present when making propylene carbonate (Comp. Ex. 5). Further, it appears that in the long term, the activity of the catalyst is higher in a case where the catalyst is pretreated with activated carbon (Ex. 2) than in a case where, when making propylene carbonate using the catalyst, such activated carbon is present (Ex. 3).

What is claimed is:

1. A process for the production of an alkylene carbonate by the reaction of an alkylene oxide with carbon dioxide in the presence of a phosphonium catalyst comprising:
   (a) introducing the alkylene oxide, carbon dioxide and phosphonium catalyst continuously into a reaction zone from which a product stream containing alkylene carbonate and phosphonium catalyst is withdrawn;
   (b) separating alkylene carbonate and a stream containing phosphonium catalyst from the product stream;
   (c) recovering the alkylene carbonate, separated in step (b), as product; and
   (d) recycling the stream containing phosphonium catalyst, separated in step (b), to the reaction zone,
   wherein the phosphonium catalyst is treated with a sorption agent comprising activated carbon.

2. The process as claimed in claim 1, wherein
   (i) the treatment with the sorption agent is carried out during the production of alkylene carbonate in the reaction zone in step (a); or
   (ii) the treatment with the sorption agent is carried out during the separation in step (b); or
   (iii) the stream containing catalyst separated in step (b) is subjected to the treatment with the sorption agent before said stream is recycled to the reaction zone; or
   (iv) the treatment is carried out in more than one of (i) to (iv).

3. The process as claimed in claim 2, wherein the sorption agent is suspended in the stream containing catalyst separated in said step (b) before said stream is recycled.

4. The process as claimed in claim 3, wherein the sorption agent is suspended in a vessel wherein the stream containing catalyst separated in said step (b) is stored before said stream is recycled.

5. The process as claimed in claim 2, wherein the sorption agent is suspended in the reaction mixture that is present in the reaction zone in step (a).

6. The process as claimed in claim 1, wherein the phosphonium catalyst is a phosphonium halide of formula $(R)_4PX$, wherein the group R contains from 1 to 12 carbon atoms and X means halide.

7. The process as claimed in claim 6, wherein the phosphonium catalyst is tetra(n-butyl) phosphonium bromide.

8. The process as claimed in claim 1, wherein the alkylene oxide is selected from the group consisting of ethylene oxide, propylene oxide, and combinations thereof.

9. The process as claimed in claim 1 wherein
   (e) the alkylene carbonate recovered as product in step (c) is contacted with an alkanol to obtain a reaction mixture containing an alkylene diol and a dialkylcarbonate; and
   (f) alkylene diol and dialkylcarbonate are recovered.

10. The process as claimed in claim 9, wherein the reaction in step (e) is performed in the presence of a heterogeneous transesterification catalyst.

11. The process as claimed in claim 9 wherein the alkanol is methanol, ethanol or isopropanol.

12. The process as claimed in claim 10 wherein the alkanol is methanol, ethanol or isopropanol.

* * * * *